United States Patent

Wolf et al.

Patent Number: 6,103,227
Date of Patent: Aug. 15, 2000

[54] LACTOBACILLUS REUTERI TO INHIBIT CRYPTOSPORIDIOSIS IN MAMMALS

[76] Inventors: Bryan Warren Wolf, 8257 Lafayette Rd., Newark, Ohio 43055; Keith Allen Garleb, 2208 Smokey View Blvd., Powell, Ohio 43081

[21] Appl. No.: 08/880,240

[22] Filed: Jun. 23, 1997

Related U.S. Application Data

[63] Continuation of application No. 08/576,274, Dec. 21, 1995, abandoned.

[51] Int. Cl.[7] .................................................. A01N 63/00
[52] U.S. Cl. ..................................... 424/93.45; 435/252.9
[58] Field of Search ....................... 435/252.9; 424/93.45

[56] References Cited

U.S. PATENT DOCUMENTS 5,352,586 10/1994 Dobrogosz et al. .
5,800,813 9/1998 Casas .

OTHER PUBLICATIONS

Axelsson et al. Microb. Ecol. in Health and Disease 2:131–136, 1989.
Alak et al. Faseb J. 10(3):A796, 1996.
Alak et al., Gastroenterology 110 (4 Suppl):A852, 1996.
Argenzio, Advances in Swine in Biomedical Res., ed. Tumbleson & Schook, Plenum Press, 1996.
Gomez et al., J. Nutr. 125:2325–2332, 1995.

*Primary Examiner*—Leon B. Lankford, Jr.
*Attorney, Agent, or Firm*—Lynn E. Barber

[57] ABSTRACT

*Cryptosporidium parvum* (the cause of cryptosporidiosis) has become one of the most common enteropathogens causing diarrhea worldwide. Symptoms associated with cryptosporidiosis are very debilitating especially in the immunocompromised subject (e.g., AIDS patient). Clinical features include severe, chronic diarrhea, abdominal cramps, fatigue, weight loss, etc. which lead to increased health care costs and increased mortality. There is disclosed herein a method of inhibiting the severity of *Cryptosporidium parvum* infection by enterally administering a therapeutically effective amount of *Lactobacillus reuteri*.

5 Claims, 1 Drawing Sheet

* Group B versus Group D (P < .05)

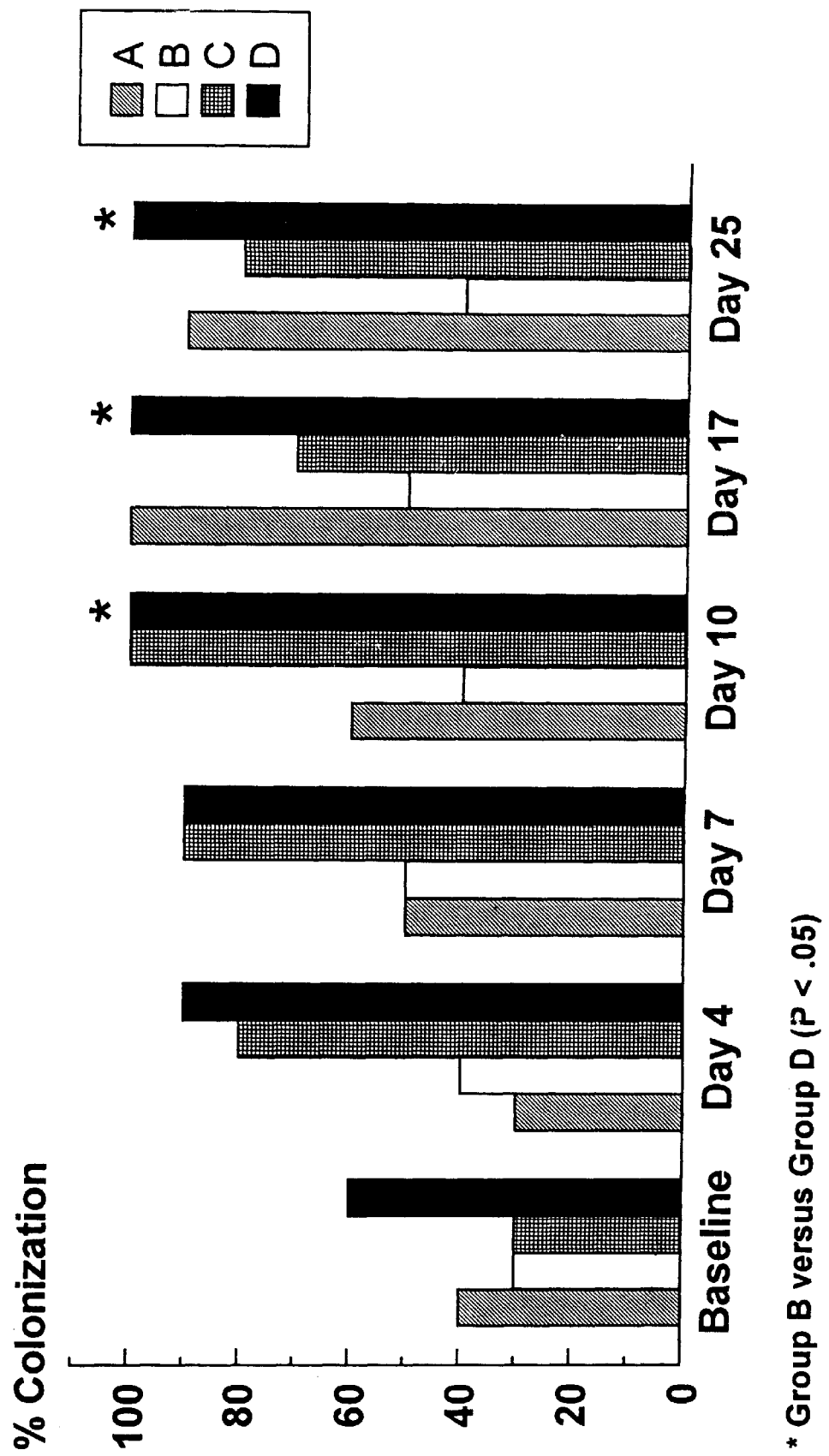

LACTOBACILLUS REUTERI TO INHIBIT CRYPTOSPORIDIOSIS IN MAMMALS

This is a continuation of application Ser. No. 08/576,274 filed Dec. 21, 1995 now abandoned.

FIELD OF THE INVENTION

This invention relates to the use of *Lactobacillus reuteri* for the inhibition of disease states associated with *Cryptosporidium parvum*.

BACKGROUND OF INVENTION

Cryptosporidiosis is caused by the protozoan parasite *Cryptosporidium parvum* (*C. parvum*). Historically, *C. parvum* had been recognized as a cause of diarrhea and mortality in young animals with an undeveloped immune system. It was not until the outbreak of acquired immunodeficiency syndrome (AIDS) that *C. parvum* was considered a significant problem in humans (Petersen, "Cryptosporidiosis in patients infected with the human immunodeficiency virus," *Clinical Infectious Diseases*, 15:903–909, 1992). Increased awareness and improved diagnostic techniques indicate that *C. parvum* may now be one of the three most important enteropathogens causing diarrheal illness worldwide (Laughon, et al., "Summary of the workshop on future directions in discovery and development of therapeutic agents for opportunistic infections associated with AIDS," *The Journal of Infectious Diseases*, 164:244–251, 1991). Pediatric outbreaks have been reported in hospitals (Navarrete, et al., "An outbreak of Cryptosporidium diarrhea in a pediatric hospital," *The Pediatric Infectious Disease Journal*, 10:248–250, 1991) and day care centers (Anonymous, "Cryptosporidiosis among children attending day-care centers—Georgia, Pennsylvania, Michigan, California, New Mexico," *Morbid. Mortal.* 33:599–601, 1984). Even more recently, a large waterborne outbreak in Milwaukee, Wisconsin affected more than 400,000 persons (MacKenzie, et al., "A massive outbreak in Milwaukee of Cryptosporidium infection transmitted through the public water supply," *New England Journal of Medicine*, 331:161–167, 1994).

*C. parvum* infection is acquired by the ingestion of oocysts which persist in the environment from the feces of infected animals or humans. During the life cycle of *C. parvum* numerous oocysts may be produced which may be excreted into the environment or remain within the host for autoinfection (Fayer, and Ungar, "Cryptosporidium spp. and cryptosporidiosis," *Microbiological Reviews*, 50:458–483, 1986). Oocysts are remarkably resistant to most common disinfectants, and routine chlorination of drinking water most likely has no effect on their viability (Current, "The biology of Cryptosporidium," *ASM News*, 54:605–611, 1988). This environmentally resistant oocyst aids in the organisms transmission through either contamination of the water supply or individual-individual contact. Some researches suggest that as few as 30 oocysts are required to infect an individual, but in the case of an immunosuppressed individual 1 oocyst may be sufficient. This may be supported by the fact that only 8 to 10 oocysts per 100 liters of water were found in the recent outbreak in Milwaukee (Schwartz, et al., "Biliary cryptosporidiosis in HIV+ patients after a waterborne outbreak in Milwaukee," *Gastroenterology*, 106 (4):A770 (abstr), 1994). Interestingly, our government recently issued the following tap-water warning: "Federal health officials have warned the nation that the daily threat of cryptosporidiosis is so widespread that anyone with a weakened immune system might want to avoid drinking water straight from the tap. The U.S. Environmental Protection Agency and Centers for Disease Control and Prevention said that people with severely weakened immune systems should take precautions such as boiling water, installing filters or using bottled water. Those at risk are people with AIDS or HIV; cancer patients; transplant patients; people with genetically weakened immune systems; and malnourished children." (The Columbus Dispatch Saturday, Jun. 17, 1995 Page 4A). To date no therapy has proven to be clinically efficacious.

Although cryptosporidiosis can be problematic for any person, its most notable impact has been among patients with human immunodeficiency virus (HIV). Clinical features include chronic (cholera-like) diarrhea, abdominal cramps, fatigue, weight loss, etc. In immunocompetent persons the onset of this disease is explosive but generally self-limiting in about two weeks. However, this condition is very debilitating to the immunosuppressed individual and is life-threatening. Recently, Blanshard and Gazzard ("Natural history and prognosis of diarrhoea of unknown cause in patients with acquired immunodeficiency syndrome (AIDS)," *Gut*, 36:283–286, 1995) have shown that *C. parvum*-associated diarrhea in AIDS patients is correlated with a significantly shorter median survival time. In their study the median survival time for patients with "pathogen negative" diarrhea was 48.7 months, which was similar to that of control patients with no diarrhea; however, median survival time was significantly longer than that of matched patients with a gastrointestinal pathogen (9.6 months). Of those patients with pathogen positive diarrhea, about 40% were determined to be caused by *C. parvum*. Others have documented the higher mortality rate in AIDS patients with cryptosporidiosis compared to noninfected AIDS patients (Gilson, et al., "Impact of a community-wide outbreak of cryptosporidiosis on patients with AIDS," *Tenth International Conference of AIDS*, 2:24 (abstr), 1994).

The true prevalence of cryptosporidiosis is not known. It has been estimated that 10 to 20 percent of AIDS patients in the U.S. have developed chronic *C. parvum* diarrhea, while the incidence is probably greater in developing countries where contaminated water supplies are of greater concern. Reported incidence rates are an underestimate of the occurrence of *C. parvum* infection because of its past unrecognized pathogenicity in humans and relative difficulty to identify.

Although numerous therapies have recently been tested, none appear to improve this debilitating condition. There is disclosed herein a method of reducing intestinal infestation by *C. parvum* by daily enteral supplementation with probiotics. Probiotics have been defined as a live microbial feed supplement which beneficially affects the host by improving its intestinal microbial balance (Fuller, "Probiotics in man and animals," *Journal of Applied Bacteriology*, 66:365–378, 1989). Some researchers believe that this normalization of the intestinal microbiota will confer the following benefits:

(a) protection against pathogens by competitive exclusion (also termed colonization resistance); (b) provision of certain nutrients and enzymatic/detoxification reactions; (c) involvement in tissue morphogenesis and peristaltic activity; and (d) interaction with the immune and endocrine systems of the host (Speck, et al., "*Lactobacillus reuteri* in food supplementation," *Food Technology*, July:90–94, 1993). Examples of probiotic organisms include several lactic acid bacteria such as the lactobacilli, streptococci, and bifidobacteria.

The more common intestinally found lactobacilli in healthy persons are *Lactobacillus reuteri* (*L. reuteri*) and *Lactobacillus acidophilus* (*L. acidophilus*). *L. reuteri* is an ubiquitous organism of man and animals. Of the intestinal lactic acid bacteria (LAB), *L. reuteri* is considered one of the most dominating species. Due to the inability of microbiologists to distinguish *L. reuteri* from *Lactobacillus fermentum* (*L. fermentum*) in the past, many researchers believe that a large percentage of LAB classified as *L. fermentum* in older literature, in reality, are strains of *L. reuteri*.

*L. reuteri* is a typical heterofermentative Lactobacillus species. Like other lactobacilli, *L. reuteri* produces acidic metabolic end-products (acetate and lactate) which have considerable antimicrobial activity. It has been recently discovered that metabolism of glycerol by *L. reuteri* can result in excretion of a metabolic intermediate, 3-hydroxypropionaldehyde (reuterin; Axelsson, "Production of a broad spectrum antimicrobial substance by *Lactobacillus reuteri*," *Microbial Ecology in Health and Disease*, 2:131–136, 1989). This compound has been shown to have antimicrobial activity against a variety of organisms to include Gram-positive and Gram-negative bacteria, yeast, molds and protozoa (Chung, et al., "In vitro studies on reuterin synthesis by *Lactobacillus reuteri*," *Microbial Ecology in Health and Disease*, 2:137–144, 1989). It is suspected that the antimicrobial activity of reuterin contributes to the survival of *L. reuteri* within the gastrointestinal ecosystem.

Likewise, *L. acidophilus* is a normal inhabitant of the human gastrointestinal tract. *L. acidophilus* is a homofermentative species, fermenting mainly hexose sugars, yielding predominantly lactic acid (85–95%). The use of *L. acidophilus* dates back to the early 20th century.

There is provided in accordance with one aspect of the present invention a method of inhibiting the infection of a mammal by *Cryptosporidium parvum* by enterally administering *Lactobacillus reuteri* in an amount which is therapeutically effective to inhibit said infection.

There is provided in accordance with another aspect of the present invention a method of inhibiting the infection of a mammal by *Cryptosporidium parvum* by enterally administering Lactobacillus reuteri in an amount which is therapeutically effective to inhibit said infection as evidenced by a reduction in the shedding of *Cryptosporidium parvum* oocysts in the feces.

There is provided in accordance with another aspect of the present invention a method of inhibiting the infection of the intestine of a mammal by the oocysts of *Cryptosporidium parvum* by enterally administering *Lactobacillus reuteri* in an amount which is therapeutically effective to inhibit said infection.

There is provided in accordance with another aspect of the present invention a method of inhibiting the infection of the intestine of a mammal by the oocysts of *Cryptosporidium parvum* by enterally administering *Lactobacillus reuteri* in an amount which is therapeutically effective to inhibit said infection as evidenced by a reduction in the shedding of *Cryptosporidium parvum* oocysts in the feces.

There is provided in accordance with another aspect of the present invention a method of increasing the resistance to *Cryptosporidium parvum* infection in an immunocompromised mammal by enterally administering *Lactobacillus reuteri* in an amount which is therapeutically effective to inhibit said infection.

There is provided in accordance with another aspect of the present invention a method of increasing the resistance to *Cryptosporidium parvum* infection in an immunocompromised mammal by enterally administering *Lactobacillus reuteri* in an amount which is therapeutically effective to inhibit said infection as evidenced by a reduction in the shedding of *Cryptosporidium parvum* oocysts in the feces.

BRIEF DESCRIPTION OF THE DRAWINGS

FIG. 1 is a graphic representation of the results of Experiment 1.

DETAILED DESCRIPTION OF INVENTION

Two experiments were conducted to determine the effect of *L. reuteri* or *L. acidophilus* on *C. parvum* infection in murine model of AIDS.

CLINICAL MODELS

Cryptosporidiosis is the only opportunistic infection of patients with AIDS for which there is no known clinically effective therapy. It is generally recognized that the best described model is that of the mouse. Several "types" of mouse models have been described, including that of the neonatal nude BALB/c mouse. This mouse develops a persistent infection; however, they become more resistant to infection after 42 days of age (Heine, et al., "Persistent Cryptosporidium infection in congenitally athymic (nude) mice," *Infection and Immunity*, 43(3):856–859, 1984). In addition, models in severe combined immunodeficient (SCID) mice and mice which receive anti-T cell antibodies have been described (Harp, et al., "Resistance of severe combined immunodeficient mice to infection with *Cryptosporidium parvum:* the importance of intestinal microflora," *Infection and Immunity*, 60(9):3509–3512, 1992; Ungar, et al., "New mouse models for chronic Cryptosporidium infection in immunodeficient hosts," *Infection and Immunity*, 58(4):961–969, 1990). One model of particular interest is the MAIDS (murine acquired immunodeficiency syndrome) infected mouse. In this model, mice are infected with murine leukemic MAIDS retroviruses in an attempt to mimic the disease course that occurs in human AIDS. Benefits of this model include a similar decrease in T-cell response and progressive splenomegaly and lymphadenopathy as in HIV/AIDS as well as a relatively rapid development of the disease (Alak et al., "Alcohol and murine acquired immunodeficiency syndrome suppression of resistance to *Cryptosporidium parvum* infection during modulation of cytokine production," *Alcoholism: Clinical and Experimental Research,* 17(3):539–544, 1993). It has been suggested that this model provides a means for studying mechanisms of resistance to *C. parvum* infection and ways to treat cryptosporidiosis (Darban, et al., "Cryptosporidiosis facilitated by murine retroviral infection with LP-BM5," *The Journal of Infectious Diseases,* 164:741–745, 1991).

An abstract presented by Famularo et al., ("Effect of lactobacilli on *Cryptosporidium parvum* infection in man and animals," *Microbial Ecology in Health and Disease,* 8(l):iii, 1995) suggested that a blend of numerous lactobacilli organisms (*S. thermophilus, L. acidophilus, L. bulgaricus, L. casei, L. plantarum* and a mixture of bifidobacteria) was effective at improving symptoms associated with cryptosporidiosis. The present invention clearly documents the ability of a single organism to inhibit the infectivity of *C. parvum*.

EXPERIMENT 1 (EXP. 1)

The objective of this study was to determine if pretreatment with *L. reuteri* could prevent or suppress *C. parvum* infection in C57BL/6 female mice immunosuppressed by LP-BM5 (LymphoProliferative-Bone Marrow 5) inoculation.

MATERIALS AND METHODS

Mice: Female C57BL/6 mice (3 to 4 weeks old) were purchased from Harlan Sprague Dawley, Inc. (Indianapolis, Ind.). Mice were housed in a micro-isolator unit with an air filtration system. Five mice were housed per cage to reduce aggressiveness. The housing facility was maintained at 20 to 22° C. and 60 to 80% relative humidity. Animals were exposed to a 12—12 hour light-dark cycle and allowed to consume water and mouse chow (Purina Company, St. Louis, Mo.) on an ad libitum basis. Mice were maintained in the facility according to standard guidelines established by the Tuskegee University Animal Care Committee (Tuskegee, Ala.) on animal health and welfare.

Inoculation of mice with LP-BM5: Mice were inoculated intraperitoneally (IP) with 0.30 milliliter (ml) of LP-BM5 murine leukemia virus (MuLv) which had an acotropic titer of 4.5 $\log_{10}$ PFU/ml (plaque-forming units/mL) in an XC-cell line. The stock of MuLV was provided by Dr. Ronald R. Watson (University of Arizona School of Medicine, Tucson, Ariz.; original source: Dr. Robert Yetter, Center for Biologics Evaluation and Research, FDA, Bethesda, Md.).

*C. parvum* inocula: Sterilized oocysts of *C. parvum* inocula were provided by Dr. James A. Harp (National Animal Disease Center, Ames, Iowa). *C. parvum* oocysts were purified from experimentally infected calves as described previously (Harp, et al., "Resistance of severe combined immunodeficient mice to infection with *Cryptosporidium parvum*: the importance of intestinal microflora," *Infection and Immunity,* 60(9):3509–3512, 1992).

Preparation of probiotic bacteria: Two mice isolates of *L. reuteri* (one stomach and one small bowel isolate, strain 4000 and 4020, respectively) were obtained from BioGaia Biologics, Inc., (Raleigh, N.C.). Stock *L. reuteri* was supplied as frozen preparations in 0.1% peptone water for inoculation of mice. The *L. reuteri* strains were grown separately and then equal colony forming units (CFU) from each strain were pooled to a final concentration of $5 \times 10^8$ CFU/ml. It is generally recognized that the mucosal colonization ability of lactobacilli (e.g., *L. reuteri*) is host specific (Lin and Savage, "Host specificity of the colonization of murine gastric epithelium by lactobacilli" FEMS Microbiology Letters 24:67–71, 1984). In order for a probiotic to compete with pathogens for adhesion receptors it must be able to colonize the gut. Thus, we used *L. reuteri* isolated from mice in our studies.

Experimental Design: A total of 40 C57BL/6 female mice (10 mice per group) were randomly assigned among one of four treatments (A, B, C or D; Table 1) after they had been immunosuppressed for 4 months by prior inoculation with LP-BM5.

TABLE 1

DESCRIPTION OF TREATMENT GROUPS FOR EXP. 1

| | Treatment | | |
|---|---|---|---|
| Group[1] | LP-BM5[2] | L reuteri[3] | C. parvum[4] |
| A | + | − | − |
| B | + | − | + |
| C | + | + | − |
| D | + | + | + |

[1]Ten mice per group (5 mice per cage).
[2]Immunosuppressed for 4 months by inoculation with LP-BM5.
[3]*L. reuteri* orally gavaged daily ($1.0 \times 10^8$ CFU per mouse) during the priming and experimental phase.
[4]Infected with *C. parvum* ($6.5 \times 10^6$ oocysts per mouse) 11 days post *L. reuteri* supplementation.

The experiment was divided into a priming phase and an experimental phase. The priming phase lasted 10 days during which 20 mice (Groups C and D) received an oral gavage of *L. reuteri* ($1 \times 10^8$ CFU in 0.2 ml) daily, the remaining 20 mice, Groups A and B, were gavaged daily with phosphate-buffered saline (PBS). Mice that received *L. reuteri* or PBS during the priming phase were similarly treated during the experimental phase while animals had ad libitum access to feed and water. During the priming phase, fecal samples were collected on day 0 (baseline), 4, and 7 for total Lactobacillus species (spp.) and *L. reuteri* enumeration. On day 10, fecal pellets were collected from all mice for the detection of shedding of *C. parvum* oocysts and enumeration of total Lactobacillus spp. and *L. reuteri*. The experimental phase was initiated on day 11 of the study during which mice (Groups B and D) were challenged with $6.5 \times 10^6$ *C. parvum* oocysts in 0.2 ml sterilized PBS. An oocyst concentration of $2.0 \times 10^5$ was previously shown to enhance growth and reduce the variability in parasite shedding in the intestinal tract of animals within the same experimental groups (Darban, et al., "Cryptosporidiosis facilitated by murine retroviral infection with LP-BM5," *The Journal of Infectious Diseases,* 164:741–745, 1991). Fecal samples were collected on day 17 and 25 for *L. reuteri,* total Lactobacillus spp. and *C. parvum* enumeration. On day 26 mice were sacrificed by ether inhalation. Afterwards, 1 to 2 centimeters (cm) of the proximal stomach, distal ileum, and colon were removed from each mouse and fixed in 10% formalin. Daily feed and water intake, initial and final body weight and the development of diarrhea were recorded.

Sampling of Lactobacillus: Fresh fecal samples (3 to 4 pellets) were weighed and placed in small sterilized vials (resistant to −70° C.). Samples were quickly frozen using alcohol and dry ice and stored at −70° C. until shipping. Samples were shipped on dry ice by overnight delivery to BioGaia Biologics, Inc. for enumeration of total Lactobacillus spp. and *L. reuteri*. *L. reuteri* and total Lactobacillus spp. were enumerated using standard anaerobic microbiological techniques and(or) techniques developed by BioGaia Biologics, Inc., as previously described (Wolf, et al., "Safety and tolerance of *Lactobacillus reuteri* in healthy adult male subjects," *Microbial Ecology in Health and Disease*, 8:41–50, 1995). Total fecal Lactobacillus spp. and *L. reuteri* counts were reported as CFU/gram (g) wet feces. In this experiment, colonization has been defined as greater than $5.0 \times 10^3$ CFU *L. reuteri*/g wet feces.

Shedding of *C. parvum* parasites: Goodgame et al., ("Intensity of infection in AIDS-associated cryptosporidiosis," *The Journal of Infectious Diseases*, 167:704–709, 1993) found a significant correlation between fecal oocyst excretion and numbers of *C. parvum* organisms seen on small bowel biopsies. They suggested that there is a threshold of infection intensity below which symptoms do not occur and that a reduction in oocyst excretion, even in the absence of complete eradication, may be a meaningful measure of drug efficacy. In this experiment *C. parvum* oocysts shed in the feces were estimated as oocysts/g feces as previously described (Alak, et al., "Alcohol and murine acquired immunodeficiency syndrome suppression of resistance to *Cryptosporidium parvum* infection during modulation of cytokine production," *Alcoholism: Clinical and Experimental Research*, 17(3):539–544, 1993). Briefly, 3 to 4 fecal pellets were collected from each mouse in pre-weighed sterile microcentrifuge tubes. The weight of each fecal sample was determined by subtracting the weight of each microcentrifuge tube from the total weight of the tubes plus the fecal contents. One ml of 10% buffered formalin solution was added to each microcentrifuge tube and the samples were either stored at room temperature or at 4° C. until analyzed. Fecal specimens were first meshed using applicator sticks, then vortexed vigorously. Suitable dilutions were made in PBS, filtered through 0.45 micrometer ($\mu$m) millipore filter (Micron Separation Inc., Westboro, Mass.) in a housing chamber (Gelman Sciences Inc., Ann Arbor, Mich.) using 5 ml syringes. The lower ends of the chambers were wrapped with PARAFILM (parafilm is a registered trademark of American Can Co.) tape and 150 microliters ($\mu$l) of a 1:8 dilution of Cryptosporidium detection reagent (Meridian Diagnostics, Inc., Cincinnati, Ohio) diluted in PBS was added to each chamber and allowed to incubate at room temperature for 1 hour and protected from light. The PARAFILM tape was removed and chambers were rinsed 3 times with PBS using 5 ml syringes. The lower ends of the chambers were sealed with PARAFILM tape and then 150 $\mu$l of counterstain reagent diluted 1:10 in PBS was added to each chamber, then incubated and rinsed. The filters containing retained oocysts on the upper surfaces of the filters were mounted on glass slides (Meridian Diagnostics, Inc.). One or 2 drops of buffered glycerin diluted 1:9 in PBS were added to the filters. Cover slips were applied and the edges sealed with clear nail polish (Pavion LTD, Nyack, N.Y.). *C. parvum* oocysts showed a characteristic bright apple green staining of the walls when observed under a leitz fluorescent microscope (Leica Inc., Chicago, Ill.) using a 40× objective lens. Taking into consideration the sample dilution factor, total weight and volume of feces, and the number of oocysts counted per filter, the oocysts shed per gram of feces were estimated. For enumeration of parasite colonization of the intestinal epithelium, 1 to 2 cm of the distal ileum was surgically removed from each mouse and rinsed in PBS. Each intestinal section was histologically stained by the conventional hematoxylin eosin method. The average number of oocysts colonized per cm length of intestinal piece were counted using a hemocytometer under phase-contrast microscopy with a 40× objective microscope lens. Infectivity scores for histologic sections were determined as number of oocysts per cm of organ.

Statistical Analyses: Because mice were handled in cages of 5 animals each, cages were nested within treatment groups. This resulted in a nested Analysis of Variance (ANOVA) model with a main effect of treatment (A, B, C, D) and a nested effect (cage within treatment). All data were examined to assess the assumption of normal distribution of the residuals by fitting the nested ANOVA model and examining the residuals with the Shapiro-Wilk test. Data that fit the assumption of normality were analyzed using the nested ANOVA model. Data that did not fit the assumption of normality were ranked and the resulting ranks analyzed using the nested ANOVA. For significant treatment effects, treatment means were compared by Tukey's HSD test. Treatment means were significant if they were different from each other at the 5% level of probability.

RESULTS—EXP. 1

Body Weights: Mice in Groups A, B, and C, had a slight decrease in body weights unlike mice in Group D whose body weights were unchanged at the end of the study. Mice in Group A had the lowest average body weight of all groups at the initiation of the study (21.45 versus 23.08, 23.66, and 23.22 g/mouse for Group B, C, and D, respectively) which may be correlated to their lower ($P<0.05$) final body weights (21.13, 22.55, 22.30, and 23.28 g/mouse for Group A, B, C, and D, respectively). Mice in Group D had the highest final body weights although this parameter was not different ($P>0.05$) from mice of Groups B and C.

Feed and water consumption: Because animals were housed 5 per cage, individual intakes could not be determined, thus these data were tabulated for descriptive purposes only. Feed intake was similar among all treatment Groups (2.80, 2.98, 2.97, and 3.19 g/mouse/day for Group A, B, C, and D, respectively). Mice supplemented with *L. reuteri* (Groups C and D) had higher water intakes (4.95 and 4.75 ml/mouse/day, respectively) than Groups A and B (3.83 and 3.98 ml/mouse/day, respectively) which were given PBS.

Shedding of *C parvum*: No *C. parvum* oocysts were detected in the feces of mice (Groups A and C) not challenged with *C. parvum*. However, mice challenged with the parasite (Groups B and D) developed persistent cryptosporidiosis (Table 2). Infection with *C. parvum* without *L.*

*reuteri* supplementation (Group B) increased (P<0.05) shedding of oocysts 7 and 14 days post infection. While there was no difference (P>0.05) in oocyst shedding between Groups B and D 7-days post infection, shedding was reduced (P<0.05) 14-days post-challenge in mice fed supplemental *L. reuteri* (Group D). Cryptosporidium parasite infection was absent from the intestinal epithelium (specifically the distal ileum) of mice of Group D. Also, no parasites were detected in the intestinal villi of uninfected mice (Groups A and C). However, significant (P<0.05) parasite burdens were detected in the intestines of mice (Group B) infected with *C. parvum* alone. Contrary to the colonization of the distal ileum, no *C. parvum* parasites were observed in tissue organs of the stomach or colon of challenged mice.

duration of the study (Table 3). Only on day 17 were statistically different levels found (Group B>Group A). The level of *L. reuteri* in the feces was similar (P>0.05) across all treatments at day 0 (baseline). On day 4, treatment groups C and D had higher (P<0.05) levels of *L. reuteri* and tended to have higher levels on day 7. However on days 10, 17, and 25 all treatment groups with the exception of Group B consistently shed high levels of *L. reuteri* in the feces. The percentage of mice colonized with *L. reuteri* is shown in FIG. 1 which shows the effect of *L. reuteri* or PBS on percentage of mice colonized by *L. reuteri* (colonization defined as greater than $5.0 \times 10^3$ CFU *L. reuteri*/g wet feces). In general, treatment groups fed supplemental *L. reuteri* had a higher percentage of animals which were colonized by the organism compared with untreated groups. In addition, on days 10, 17 and 25 mice in Group D had a higher (P<0.05) percent colonization than mice in Group B.

TABLE 3

Effects of feeding supplemental *L. reuteri* on fecal level of total Lactobacillus spp. and *L. reuteri* ($\log_{10}$ CFU/g ± SEM) of C57BL/6 mice immunosuppressed by prior inoculation with LP-BM5 and challenged (+/−) with *C. parvum*.

| Group[1] | Day 0 | Day 4 | Day 8 | Day 10 | Day 18 | Day |
|---|---|---|---|---|---|---|
| | Total Lactobacillus spp.--days post *L. reuteri* feeding | | | | | |
| A | 8.90 ± 0.11 | 9.11 ± 0.12 | 9.07 ± 0.12 | 9.25 ± 0.06 | 8.49 ± 0.17[b] | 9.15 ± |
| B | 8.83 ± 0.11 | 8.92 ± 0.06 | *9.07 ± 0.07 | *9.00 ± 0.08 | 9.18 ± 0.10[a] | **9.07 |
| C | 8.71 ± 0.11 | 9.77 ± 0.12 | 9.33 ± 0.08 | 9.22 ± 0.15 | **9.01 ± 0.10[a,b] | **9.07 |
| D | 8.60 ± 0.08 | 9.70 '5 0.11 | 9.35 ± 0.15 | 9.12 ± 0.20 | 8.93 ± 0.13[a,b] | 8.98 ± |
| | *L. reuteri* | | | | | |
| A | 4.85 ± 0.48 | 4.67 ± 0.51[b] | 5.29 ± 0.60[a,b] | 6.12 ± 0.68 | 6.88 ± 0.24 | 7.15 ± |
| B | 4.25 ± 0.28 | 4.65 ± 0.39[b] | *5.17 ± 0.47[b] | *5.29 ± 0.65 | 5.76 ± 0.69 | **5.01 |
| C | 4.33 ± 0.34 | 6.79 ± 0.60[a] | 6.75 ± 0.39[a,b] | 8.20 ± 0.19 | **6.66 ± 0.51 | **7.64 |
| D | 5.13 ± 0.39 | 7.48 ± 0.45[a] | 6.88 ± 0.49[a] | 7.97 ± 0.23 | 7.26 ± 0.18 | 8.16 ± |

[1]Ten mice per group (5 per cage) unless otherwise noted: * = 9, ** = 8.
[a,b]Values within the same column with unlike superscript letters differ (P < .05).

TABLE 2

Effects of feeding supplemental *L. reuteri* on shedding of oocysts (oocysts × $10^3$/g ± SEM) in the feces and colonization of the distal ileum (oocysts/cm intestine ± SEM) epithelium of C57BL/6 mice immunosuppressed by prior inoculation with LP-BM5 and challenged (+/−) with *C. parvum*.

| | Days post *L. reuteri* feeding | | | |
|---|---|---|---|---|
| Group[1] | Day 10[2] | Day 17[3] | Day 25[4] | Ileum |
| A | 0.00 ± 0.00 | 0.00 ± 0.00[b] | 0.00 ± 0.00[c] | 0.00 ± 0.00[b] |
| B | 0.00 ± 0.00 | 1.58 ± 0.24[a] | 9.19 ± 4.29[a] | *4.00 ± 1.13[a] |
| C | 0.00 ± 0.00 | *0.00 ± 0.00[b] | *0.00 ± 0.00[c] | *0.00 ± 0.00[b] |
| D | 0.00 ± 0.00 | 1.34 ± 0.33[a] | 0.46 ± 0.13[b] | 0.00 ± 0.00[b] |

[1]Ten mice per group (5 per cage) unless otherwise noted: * = 8.
[2]Corresponds to baseline sample taken immediately prior to *C. parvum* challenge.
[3]Corresponds to day 7 post *C. parvum* challenge.
[4]Corresponds to day 14 post *C. parvum* challenge.
[a,b,c]Values within the same column with unlike superscript letters differ (P < .05).

Lactobacillus colonization: Fecal levels of total Lactobacillus spp. were similar across all treatments throughout the

DISCUSSION EXP. 1

Infection of mice with LP-BM5 induced murine AIDS syndrome with no latent phase. This syndrome had many similarities to human AIDS. Symptoms included progressive splenomegaly, lymphadenopathy and increased susceptibility to *C. parvum* infection. Unlike human AIDS which is associated with weight loss and sometimes life threatening diarrhea, murine AIDS was not associated with significant weight loss or diarrhea.

Treatment of mice with *L. reuteri* increased (P<0.05) the intestinal population of *L. reuteri* (Groups C and D) compared to mice that did not receive supplemental *L. reuteri* (Groups A and B) on day 4 post *L. reuteri* feeding. There was an inverse relationship between *L. reuteri* population and clearance of *C. parvum* parasites from the intestinal tract in treatment Groups B and D. Thus, mice infected with *C. parvum* and concomitantly fed supplemental *L. reuteri* (Group D) cleared (P<0.05) parasite loads (Table 2) compared with those that were infected with *C. parvum* alone (Group B). At 14 days post Cryptosporidium challenge, no parasites were detected on the intestinal tract epithelium of these mice (Group D). On the contrary, control mice challenged with Cryptosporidium, were unable to clear the infection 14 days post challenge. This demonstrates a heretofore unrecognized prophylactic role of L. reuteri in inhibiting the growth of C. parvum in the intestinal mucosa. The mechanisms by which L. reuteri inhibit the proliferation of C. parvum are not known. It is speculated that L. reuteri may inhibit the proliferation of other bacteria and parasites in the gut microbiota by competition for binding sites or by the secretion of inhibitory products towards other organisms. This study provides evidence that L. reuteri is beneficial for the inhibition of opportunistic infections such as C. parvum, especially in immunocompromised individuals.

EXPERIMENT 2 (EXP. 2)

A second experiment was conducted to determine if pre-treatment with L. reuteri or L. acidophilus could prevent or inhibit C. parvum infection in mice infected with MAIDS.

MATERIALS AND METHODS

Mice: Mice were obtained and cared for in the same manner as explained for Exp. 1, except that mice were ear notched in order to identify each animal.

Inoculation of mice with LP-BM5: Same as Exp. 1

Cryptosporidium inocula: Same as Exp. 1

Preparation of probiotic bacteria: L. reuteri was prepared as explained in Exp. 1. A human isolate of L. acidophilus (strain NCFM) was obtained from BioGaia Biologics, Inc. The L. acidophilus was prepared with a final concentration of $5 \times 10^8$ CFU/mL. Probiotic ingredients were stored frozen in 0.1% peptone water until needed.

Experimental Design: In this experiment sixty C57BL/6 female mice (15 per group) were randomly assigned among one of four treatments (E, F, G, and H; Table 4). Again, the study was divided into a priming and experimental phase.

TABLE 4

DESCRIPTION OF TREATMENT GROUPS FOR EXP. 2

| Group[1] | LP-BM5[2] | L reuteri[3] | L acidophilus[4] | C. parvum[5] |
|---|---|---|---|---|
| E | + | − | − | − |
| F | + | − | − | + |
| G | + | + | − | + |
| H | + | − | + | + |

[1]Fifteen mice per group (5 mice per cage).
[2]Immunosuppressed for 4 months by inoculation with LP-BM5.
[3]L reuteri orally gavaged daily ($1.0 \times 10^8$ CFU per mouse) during the priming and experimental phase.
[4]L. acidophilus orally gavaged daily ($1.0 \times 10^8$ CFU per mouse) during the priming and experimental phase.
[4]Infected with C. parvum ($1.4 \times 10^5$ oocysts per mouse) 14 days post probiotic supplementation.

During the priming phase (13 days in length), 30 mice (Group E and F) received a daily oral gavage of 0.1% peptone water (0.2 ml), 15 mice (Group G) received a daily oral gavage of L. reuteri ($1 \times 10^8$ CFU in 0.2 ml), and 15 mice (Group H) received a daily oral gavage of L. acidophilus ($1 \times 10^8$ CFU in 0.2 ml). Mice continued to be orally gavaged daily with their respective treatments throughout the experiment. During the priming phase, fecal samples were taken on day 1 (baseline) and 8 for total Lactobacillus spp. and L. reuteri enumeration. An attempt to determine fecal levels of L. acidophilus was made on some samples in Group H; however, the method was too cumbersome and variable, thus the L. acidophilus analysis was not completed. On day 13 fecal samples were collected from all mice for the detection of C. parvum shedding and total Lactobacillus spp. and L. reuteri enumeration. The experimental phase was initiated on day 14 during which animals (Group F, G, and H) were challenged with ($1.4 \times 10^5$ oocysts) C. parvum. Fecal samples were collected on day 21 and 28 (7 and 14 days postchallenge) for C. parvum, total Lactobacillus spp. and L. reuteri enumeration. On day 28 mice were sacrificed by ether inhalation. Afterwards, 1 to 2 cm of the proximal stomach, distal ileum, and colon were removed for detection of C. parvum on the gut epithelium. Daily documentation of feed and water intake for each cage, and diarrhea were noted. In addition, initial and final body weights were recorded.

Sampling of Lactobacillus: Same as Exp. 1. Due to variation in the detection limits of Exp. 2, colonization was defined as greater than $2.7 \times 10^4$ CFU L. reuteri/g wet feces.

Shedding of C. parvum parasites: Same as Exp. 1 except that infectivity scores for histological sections of the distal ileum were determined as number of oocysts per 25 intestinal villi.

Statistical Analyses: As in Exp. 1, animals were not handled individually but rather in cages of 5 animals each, thus cages were nested within treatment group. This results in a nested Analysis of Variance model with a main effect of treatment (E, F, G, and H) and a nested effect (cage within treatment). Statistical methods were similar to that described for Exp. 1. Again, results were considered to be statistically significant if the significance level was less than 5 percent.

RESULTS—EXP. 2

Body Weights: Initial (21.80, 22.82, 22.03, and 22.46 g/mouse for Group E, F, G, and H, respectively) and final (22.18, 23.01, 22.28, and 23.07 g/mouse for Groups E, F, G, and H, respectively) body weights were similar (P>0.05) among all treatments. In general, mice showed a slight increase in body weight over the duration of the study. Feed and water consumption: Feed (3.33, 3.40, 3.33, and 3.40 g/mouse/day for Groups E, F, G, and H, respectively) and water (3.92, 3.97, 3.98, and 3.96 mL/mouse/day for Groups E, F, G, and H, respectively) intake were similar among treatments.

Shedding of C. parvum: No C. parvum oocysts were detected in the feces of mice that were not challenged with C. parvum (Group E). As in Exp. 1, challenged animals developed persistent cryptosporidiosis (Table 5). Day-7 post-challenge, mice which were supplemented with L. reuteri or L. acidophilus (Groups G and H, respectively) shed fewer (P<0.05) C. parvum oocysts compared to challenged controls (Group F). On day-14 post-challenge only mice supplemented with L. acidophilus (Group H) had lower (P<0.05) fecal levels of C. parvum oocysts compared to challenged controls (Group F); however, this level was not different (P>0.05) from L. reuteri supplemented animals (Group G). Unlike Exp. 1, intestinal infestation of the ileal villi was noted in probiotic supplemented, C. parvum chal lenged mice. Fewer oocysts were detected on the villi of *L. acidophilus* (Group H) supplemented animals with no difference (P>0.05) from control non-challenged animals being detected. However, there was no difference (P>0.05) from the other challenged groups (Group F and G). As in Exp. 1, no oocyst colonization was noted in the proximal stomach or colon of mice.

on day-7 post *C. parvum* challenge than the control, challenged animals (Table 3)

Unfortunately, fecal analysis for *L. acidophilus* was too difficult, thus the analysis was not completed. Mice supplemented with *L. acidophilus* shed fewer (P<0.05) oocysts 7 and 14 days post *C. parvum* challenge compared to challenged controls; however, this reduction was not different

TABLE 5

Effects of feeding supplemental *L. reuteri* or *L. acidophilus* on shedding of oocysts ($\log_{10}$ oocysts/g ± SEM) in the feces and colonization of the distal ileum (oocysts/25 intestinal villi ± SEM) epithelium of C57BL/6 mice immunosuppressed by prior inoculation with LP-BM5 and challenged (+/−) with *C. parvum*

| Group[1] | Days post probiotic feeding | | | Ileum |
|---|---|---|---|---|
| | Day 13[2] | Day 21[3] | Day 28[4] | Day 28[4] |
| E | 0.00 ± 0.00 | **0.00 ± 0.00[c] | **0.00 ± 0.00[c] | **0.00 ± 0.00[b] |
| F | 0.00 ± 0.00 | 4.32 ± 0.17[a] | 3.88 ± 0.32[a] | 2.33 ± 0.81[a] |
| G | 0.00 ± 0.00 | 2.96 ± 0.43[b] | 3.50 ± 0.29[a,b] | 213 ± 0.58[a] |
| H | 0.00 ± 0.00 | *2.35 ± 0.52[b] | *1.95 ± 0.54[b] | *1.79 ± 0.71[a,b] |

[1] Fifteen mice per gruop (5 per cage) unless otherwise noted: * = 14, ** = 13.
[2] Corresponds to baseline sample taken immediately prior to *C. parvum* challenge.
[3] Corresponds to day 7 post *C parvum* challenge.
[4] Corresponds to day 14 post *C parvum* challenge.
[a,b,c] Values within the same column with unlike superscript letters differ (P < .05).

Lactobacillus colonization: Fecal levels of total Lactobacillus spp. was similar among all treatments throughout the trial (Table 6). Statistical differences were found only on day 13 and 28. Fecal levels of *L. reuteri* were similar among treatments at baseline, day 8 and 13; however, levels were about 2 logs higher in Exp. 2 than baseline levels of Exp. 1. Generally, *L. reuteri* levels were high in all treatments with statistical differences being noted on day 21 and 28 (see Table 6).

from *L. reuteri* supplemented animals. This experiment suggests that *L. acidophilus* has a similar beneficial effect for the prevention of cryptosporidiosis as that of *L. reuteri*.

CONCLUSIONS

Overall, prophylactic supplementation with probiotics (specifically *L. reuteri* and *L. acidophilus*) reduces the infectivity of *C. parvum* of a mammal in this murine AIDS

TABLE 6

Effects of feeding supplemental *L. reuteri* or *L. acidophilus* on fecal level of total Lactobacillus spp. and *L reuteri* ($\log_{10}$ CFU/g ± SEM) of C57BL/6 mice immunosuppressed by prior inoculation with LPO-BM5 and challenged (+/−) with *C. parvum*.

| Group[1] | Day 1 | Day 8 | Day 13 | Day 21 | Day 28 |
|---|---|---|---|---|---|
| | Total Lactobacillus spp.--days post probiotic feeding | | | | |
| E | 8.48 ± 0.18 | 8.54 ± 0.10 | 9.89 ± 0.15[a] | **9.58 ± 0.11 | **9.91 ± 0.12[b] |
| F | 8.43 ± 0.12 | 9.35 ± 0.15 | 8.80 ± 0.15[b] | 10.14 ± 0.11 | 10.66 ± 0.05[a] |
| G | 8.48 ± 0.21 | 9.22 ± 0.09 | 9.71 ± 0.11[a] | **10.15 ± 0.20 | *10.94 ± 0.08 |
| | *L. reuteri* | | | | |
| E | 5.90 ± 0.44 | 6.58 ± 0.39 | 6.45 ± 0.58 | **4.90 ± 0.56[b] | **8.09 ± 0.17[b] |
| F | 6.44 ± 0.20 | 6.,04 ± 0.47 | 4.72 ± 0.50 | 7.70 ± 0.32[a,b] | 8.52 ± 0.13[b] |
| G | 6.30 ± 0.36 | 7.76 ± 0.19 | 6.15 ± 0.39 | 7.79 ± 0.57[a] | 9.72 ± 0.11[a] |
| H | 6.23 ± 0.43 | 6.58 ± 0.33 | 6.97 ± 0.49 | **8.33 ± 0.18[a] | *8.42 ± 0.57[a,b] |

[1] Fifteen mice per group (5 per cage) unless otherwise noted: * = 14, ** = 13.
[a,b] Values within the same column with unlike superscript letters differ (P < .05).

DISCUSSION—EXP. 2

Animals in this trial were naturally colonized with *L. reuteri*; however, baseline *L. reuteri* levels were much higher than reported in Exp. 1. Due to this fact, the higher fecal level of *L. reuteri* can not be correlated with the lower *C. parvum* oocyst shedding (day-7). Regardless, animals supplemented with *L. reuteri* shed fewer (P<0.05) oocysts model as evidenced by a reduction in the shedding of *C. parvum* oocysts in the feces. Whether *L. reuteri* and *L. acidophilus* possess a synergistic effect warrants further study. These experiments have documented a benefit of probiotics (specifically *L. reuteri* and *L. acidophilus*) for the prevention of cryptosporidiosis in an immunosuppressed population. The level of *L. reuteri* fed to mice in our experiments was 1×10⁸ CFU per mouse per day. On a body weight basis this would correspond to approximately $3 \times 10^{11}$ CFU per day for a 70 kilogram person. The present invention may be practiced by feeding at least, but not limited to, $1 \times 10^8$ CFU per day per subject. Clinical evaluation of the use of *L. reuteri* for the inhibition of *C. parvum* in AIDS patients are planned in the near future.

The present invention, as supported by the foregoing experiments and discussion thereof, is a method of inhibiting the infection of a mammal by *Cryptosporidium parvum* by enterally administering Lactobacillus reuteri in an amount which is therapeutically effective to inhibit such an infection. That is to say, the present invention is a method of inhibiting the infection of the intestine of a mammal by the oocysts of *Cryptosporidium parvum* by enterally administering *Lactobacillus reuteri* in an amount which is therapeutically effective to inhibit said infection. Furthermore, the present invention is a method of increasing the resistance to *Cryptosporidium parvum* infection in an immunocompromised mammal by enterally administering *Lactobacillus reuteri* in an amount which is therapeutically effective to inhibit such an infection. The inhibition of the infection of a mammal by *Cryptosporidium parvum*, may be evidenced by a reduction in the shedding of *Cryptosporidium parvum* oocysts in the feces of the mammal being treated. The resistance to *Cryptosporidium parvum* infection in an immunocompromised mammal may also be evidence by a reduction in the shedding of *Cryptosporidium parvum* oocysts in the feces of the mammal being treated.

The *Lactobacillus reuteri* may be enterally administered by any suitable means, including but not limited to:

(a) adding the Lactobacillus reuteri to a liquid via an osmotic pump and thereafter enterally administering the resultant liquid;

(b) enterally administered by enterally administering a capsule containing the *Lactobacillus reuteri*;

(c) consuming a yogurt containing *Lactobacillus reuteri* at a concentration of at least $1.0 \times 10^8$ CFU *Lactobacillus reuteri*/g;

(d) consuming a milk product containing *Lactobacillus reuteri* at a concentration of at least $1.0 \times 10^8$ CFU *Lactobacillus reuteri*/ml;

(e) consuming a condiment that contains $1.0 \times 10^8$ to $1.0 \times 10^{12}$ CFU *Lactobacillus reuteri*/g, for example by combining the condiment with a food and then consuming the food;

(f) consuming a dosage unit comprising *Lactobacillus reuteri* and at least one excipient, for example by combining the dosage unit with a food and then consuming the food, dosage unit being for example a tablet, capsule, powder or liquid which contains *Lactobacillus reuteri*;

(g) consuming a food product containing at least $1.0 \times 10^8$ CFU *Lactobacillus reuteri*/g.

(h) consuming a suspension containing *Lactobacillus reuteri*;

(i) enterally administering a tablet containing the *Lactobacillus reuteri*; and (j) ingesting as an osmotic pump which will deliver the Lactobacillus reuteri into the gastrointestinal tract.

An enterally administrable product which may be used in the practice of the present invention is an enterally administrable product containing *Lactobacillus reuteri* in an amount which is therapeutically effective to inhibit the infection of a mammal to which it is administered by *Cryptosporidium parvum*. Examples of such products include, but are not limited to:

(a) a capsule containing the *Lactobacillus reuteri*;

(b) a yogurt containing at least $1.0 \times 10^8$ CFU *Lactobacillus reuteri*/g;

(c) a milk product containing at least $1.0 \times 10^8$ CFU *Lactobacillus reuteri*/ml;

(d) a condiment containing at least $1.0 \times 10^8$ CFU *Lactobacillus reuteri*/g;

(e) a tablet containing at least $1.0 \times 10^8$ CFU *Lactobacillus reuteri*/g;

(f) a suspension containing at least $1.0 \times 10^8$ CFU *Lactobacillus reuteri*/ml;

(g) a condiment which contains *Lactobacillus reuteri*, said condiment being suitable for combining with a food;

(h) a dosage containing *Lactobacillus reuteri* unit with at least on excipient;

(i) an osmotic pump which may be used to add the *Lactobacillus reuteri* to a liquid;

(j) an osmotic pump which may be consumed enterally and delivers the *Lactobacillus reuteri* directly into the gastrointestinal tract; and (k) a food product which contains the *Lactobacillus reuteri*.

We claim:

1. A method of inhibiting the infection of a mammal by *Cryptosporidium parvum* by enterally administering *Lactobacillus reuteri* that colonizes the gut of the mammal in an amount which is therapeutically effective to inhibit said infection.

2. A method of inhibiting the infection of a mammal by *Cryptosporidium parvum* by enterally administering *Lactobacillus reuteri* that colonizes the gut of the mammal in an amount which is therapeutically effective to inhibit said infection as evidenced by a reduction in the shedding of *Cryptosporidium parvum* oocysts in the feces.

3. A method of inhibiting the infection of the intestine of a mammal by the oocysts of *Cryptosporidium parvum* by enterally administering *Lactobacillus reuteri* that colonizes the gut of the mammal in an amount which is therapeutically effective to inhibit said infection.

4. A method of increasing the resistance to *Cryptosporidium parvum* infection in an immunocompromised mammal by enterally administering *Lactobacillus reuteri* that colonizes the gut of the mammal in an amount which is therapeutically effective to inhibit said infection.

5. A method of inhibiting the infection of a mammal by *Cryptosporidium parvum* by enterally administering *Lactobacillus reuteri* in an amount which is therapeutically effective to inhibit said infection as evidenced by reduction of diarrhea.

* * * * *